United States Patent
Battista et al.

(10) Patent No.: US 10,865,426 B2
(45) Date of Patent: Dec. 15, 2020

(54) SEQUENTIALLY-FED PROCESS FOR ENZYMATIC HYDROLYSIS WITH ADDITIONS OF PRE-TREATED SUBSTRATE INCREASINGLY SPREAD OUT OVER TIME

(71) Applicant: IFP Energies Nouvelles, Rueil-Malmaison (FR)

(72) Inventors: Federico Battista, Lyons (FR); Romain Rousset, Lyons (FR); Melanie Gomez Almendros, Lyons (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 16/143,562

(22) Filed: Sep. 27, 2018

(65) Prior Publication Data
US 2019/0093133 A1 Mar. 28, 2019

(30) Foreign Application Priority Data
Sep. 28, 2017 (FR) ..................................... 17 59033

(51) Int. Cl.
| | |
|---|---|
| *C12P 7/10* | (2006.01) |
| *C13K 1/02* | (2006.01) |
| *C12P 19/14* | (2006.01) |
| *C12P 7/14* | (2006.01) |
| *C12P 19/02* | (2006.01) |

(52) U.S. Cl.
CPC .................. *C12P 7/10* (2013.01); *C12P 7/14* (2013.01); *C12P 19/02* (2013.01); *C12P 19/14* (2013.01); *C13K 1/02* (2013.01); *C12P 2201/00* (2013.01); *C12P 2203/00* (2013.01)

(58) Field of Classification Search
CPC ...................................................... C12P 19/02
See application file for complete search history.

(56) References Cited

U.S. PATENT DOCUMENTS

2016/0333382 A1   11/2016   Lali

FOREIGN PATENT DOCUMENTS

WO   2015107415 A1   7/2015

OTHER PUBLICATIONS

Fan et al. Bioprocess Biosyst Eng., 2007, 30:27-34.*
Cardona, et al. Bioresource Technology, 2015, 198:488-496.*
Search Report in corresponding FR application 1759033 dated Jun. 18, 2018 (pp. 1-5).
Rosgaard L et al: Effects of substrate 1-14 loading on enzymatic hydrolysis and viscosity of pretreated barley straw ,Applied Biochemistry and Biotechnology , Part A: Enzyme Engineering and Biotechnology, Humana Press Inc, New York, vol • 143, No. 1, (Oct. 1, 2007), pp. 27-40, XP002668850, ISSN: 0273-2289, DOI: 10.1007/s12010-007-0028-1.
Olofsson et al: Designing simultaneous saccharification and fermentation for improved xylose conversion by a recombinant strain of *Saccharomyces cerevisiae* , Journal of Biotechnology. Elsevier. Amsterdam. NL. vol. 134. No. 1-2. (Jan. 17, 2008). pp. 112-120. XP022500133. ISSN: 0168-1656.
Modenbach Alicia A et al: Enzymatic hydrolysis of biomass at high-solids loadings—A review . Biomass and Bioenergy. vol. 56. 2013. pp. 526-544. XP028684730. ISSN: 0961-9534, DOI: 10.1016/J. BIOMBIOE.2013.05.031.
Sotaniemi Ville-Hermann et al: Controlled feeding of lignocellulosic substrate enhances the performance of fed-batch enzymatic hydrolysis in a stirred tank reactor, Biomass and Bioenergy, Pergamon, Amsterdam, NL, vol. 91, Jun. 6, 2016 (Jun. 6, 2016), pp. 271-277, XP029619781, ISSN: 0961-9534.
Zhang X et al: High consistency enzymatic hydrolysis of hardwood substrates,Bioresource Technology, Elsevier, Amsterdam, NL, vol . 100, No. 23, (Dec. 1, 2009), pp. 5890-5897, XP026469499, ISSN: 0960-8524.
Federico Battista et al: Enzymatic hydrolysis at high dry matter content: The influence of the substrates physical properties and of loading strategies on mixing and energetic consumption , Bioresource Technology, vol. 250, (Nov. 20, 2017), pp. 191-196, XP055480461.

* cited by examiner

*Primary Examiner* — Bin Shen
(74) *Attorney, Agent, or Firm* — Millen White Zelano and Branigan, PC; Csaba Henter

(57) ABSTRACT

The present invention relates to a sequentially fed process for enzymatic hydrolysis in which, under agitation, a pre-treated lignocellulosic substrate is brought into contact with water and with enzymes in a reactor, said process being characterised in that the sequential addition to the reactor of the pre-treated lignocellulosic substrate is carried out increasingly spread out over time, in order to obtain a predetermined final content of dry matter.

17 Claims, 3 Drawing Sheets

SEQUENTIALLY-FED PROCESS FOR ENZYMATIC HYDROLYSIS WITH ADDITIONS OF PRE-TREATED SUBSTRATE INCREASINGLY SPREAD OUT OVER TIME

FIELD OF THE INVENTION

The present invention relates to a process for enzymatic hydrolysis from a pre-treated lignocellulosic substrate in sequential supply mode, as defined below, allowing the conversion of the cellulose into glucose. The glucose can then be used in various further steps such as, for example, in a fermentation step for the production of alcohols, or for the production of intermediates for chemistry.

PRIOR ART

The development of economically viable processes for upgrading lignocellulosic biomass is currently a "hot topic". The increasing scarcity of fossil resources and competition with food supplies have resulted in a search for novel pathways to the production of biofuels and chemical intermediates.

Since the 1970s, the transformation of lignocellulosic biomass after hydrolysis of the constituent polysaccharides into sugars has been the subject of many studies.

Lignocellulosic biomass is characterised by a complex structure constituted by three principal polymers: cellulose, hemicelluloses and lignin, the proportions of which vary as a function of the species of lignocellulosic biomass. A typical but not limiting composition is as follows: the cellulose is present in a quantity in the range 35% to 50%, the hemicelluloses, which are polysaccharides essentially constituted by pentoses and hexoses, are present in a quantity in the range 20% to 30% and the lignins are in a quantity in the range 15% to 25% by weight. Degradation of the biomass proves to be difficult, since the polysaccharides of the plant wall (cellulose and hemicelluloses) are intimately associated with lignin, which provides the walls with rigidity.

Of these three polymers, cellulose is the principal source of sugars, as it is constituted by glucose; this latter is readily upgraded.

Conventionally, processes for upgrading biomass by a biochemical pathway comprise a plurality of steps. A first step is collection and transport of the lignocellulosic biomass to a biomass transformation centre. The second step is the pre-treatment or pre-hydrolysis of the biomass, which renders the cellulose accessible to the enzymes and thus capable of producing a pre-treated lignocellulosic substrate. The third step, enzymatic hydrolysis, means that, because a solution of cellulolytic and hemicellulolytic enzymes produced by microorganisms and known as an enzymatic cocktail is used, cellulose is transformed into glucose. This glucose may then be upgraded to intermediate products, for example to ethanol, during a fourth step of fermentation, generally by the yeast *Saccharomyces cerevisiae*, or to an acetone, butane, ethanol (ABE) mixture by fermentation by the yeast *Clostridium acetobutylicum*. A fifth step, distillation, then means that the molecules obtained can be concentrated. The glucose can also be upgraded to biofuels (hydrogen, methane).

One of the key steps is thus the enzymatic hydrolysis. In the enzymatic hydrolysis step, said pre-treated lignocellulosic substrate must be mixed with a liquid solution containing the cellulolytic and hemicellulolytic enzymes. Since the aim is to obtain a high concentration of sugars, the enzymatic hydrolysis step must be carried out at high concentrations of pre-treated lignocellulosic substrate, that is to say at a high content of dry matter. It has been estimated that the process is economically viable when a minimum concentration of sugars of 8% by weight is produced during the enzymatic hydrolysis, which corresponds to a content of dry matter of approximately 15% by weight (McIntosh, S., Zhang, Z., Palmer, J., Wong, H., Doherty, W. O. S., Vancov, T., 2016. Pilot-scale cellulosic ethanol production using eucalyptus biomass pre-treated by dilute acid and steam explosion. Biofuels, bioproducts and biorefining 10 (4), 346-358). Working at a high content of dry matter also allows a reduction in the volume of the reactor and, as a consequence, a reduction in the financial and energy costs of the process (Larsen, J., Ostergaard Petersen, M., Thirup, L., Wen Li, H., Krogh Iversen, F., 2008. The IBUS process of lignocellulosic bioethanol close to a commercial reality. Chem. Eng. Technol. 31, 765-722).

However, intimate mixing of the pre-treated lignocellulosic substrate with said liquid solution containing the cellulolytic and hemicellulolytic enzymes can prove difficult when the contents of dry matter are high. In fact, the start of the enzymatic hydrolysis at a high content of dry matter poses particular problems of mixing and homogenisation. The reaction medium is very pasty and viscous which calls for special agitation that is much more complex than that necessary at the end of hydrolysis when the reaction mixture has become more liquid.

Generally speaking, enzymatic hydrolysis can be carried out in discontinuous or continuous reactors. In a discontinuous, or batch, process, all the components, including the substances controlling the pH, are placed in the reactor at the start of the hydrolysis. During the process of hydrolysis, nothing is added to or removed from the reactor. In a continuous process, there are both incoming and outgoing flows, but the reaction volume is kept constant.

In another configuration of the process, also referred to as a sequentially fed, or fed-batch mode process, nothing is removed from the reactor during the process, but the substrate is progressively added in a sequential fashion to the reactor during the period of hydrolysis without removing any hydrolysate. It has been found that with this type of feeding of the substrates it is possible to overcome effects such as the inhibition by the substrate of the product yield. As and when the reaction progresses, the mixture becomes increasingly liquid and it is possible to add fresh substrate in order to increase the dry matter content. It is then possible to reach high substrate concentrations and advantageously of between 17 and 30% by weight of dry matter.

Enzymatic hydrolysis processes with continuous feed are known from the prior art (Mondebach, A. A., Nokel, S. E., 2013. Enzymatic hydrolysis of biomass at high-solids loadings—A Review. Biomass and Bioenergy 56, 526-544).

Similarly, patent application US2010/330638A describes a fed-batch mode of supply at the enzymatic hydrolysis step, indicating that tests allow a determination of the quantity of biomass that can be added to each batch. It is therefore necessary to carry out tests prior to the enzymatic hydrolysis steps each time the substrate type is changed.

Application WO2016/062646 describes a process for the preparation of a sugar and/or fermentation product from lignocellulosic material, which comprises a number of steps of enzymatic hydrolysis, the first of which is in fed-batch mode.

Patent application US 2010/0255554 describes a process for the hydrolysis of lignocellulosic biomass in fed batch mode, in which the functional parameters of the process are adjusted by controlling the volume of the reactor and/or the frequency of addition of the pre-treated lignocellulosic biomass feed and optionally the addition of enzymes, and the volume and/or concentration of sugars produced in the reactor. In particular, the pre-treated lignocellulosic biomass feed is always added at the same frequency to the reactor.

The applicant has developed an improved process of enzymatic hydrolysis with sequential feed (fed-batch) allowing high yields of glucose to be obtained while reducing energy consumption by the process and the mixing time.

More specifically, the present invention relates to a sequentially fed process for enzymatic hydrolysis in which, under agitation, at least one pre-treated lignocellulosic substrate is brought into contact with water and with enzymes in a reactor, said process being characterised in that the sequential addition to the reactor of the pre-treated lignocellulosic substrate is carried out increasingly spread out over time, in order to obtain a predetermined final content of dry matter.

When the pre-treated lignocellulosic substrate, and preferably also the enzymes, are injected into a process for enzymatic hydrolysis with sequential feeding (fed-batch) that is increasingly spread out over time, an increase in glucose yield is observed together with a drop in energy consumption compared with a fed-batch mode in which the substrate is added at constant intervals of time.

Moreover, when the enzymes are added in the same way, that is to say sequentially and distributed over time, and preferably at the same time as the substrate, a synergy effect is noticed on the glucose yield which is not seen when all the enzymes are added at the start of the hydrolysis.

An advantage of the present invention is that it provides a process of enzymatic hydrolysis in which the glucose yield is improved.

Another advantage of the present invention is that it provides a process of enzymatic hydrolysis in which, thanks to the fed-batch technique but which is distributed over time, the problems of mixing and viscosity are seen less often, if at all. In fact, thanks to the progressive increase in the content of dry matter, the mixing takes place easily with each addition of substrate, allowing on the one hand a reduction in the consumption of energy by the stirrers and/or the use of less complex stirrers, such as inclined blade impellers or marine impellers.

Moreover, a further advantage of the present invention is the provision of a process of enzymatic hydrolysis in which the speed of rotation of the stirrer is low, which is important for maintaining enzymatic activity (Mhlongo S I, Haan R, Viljoen-Bloom M, Zyl W H. Lignocellulosic hydrolysate inhibitors selectively inhibit/deactivate cellulase performance (2015). Enzyme and Microbial Technology, 81: 16-22).

Moreover, the process according to the invention is suitable when a number of substrates of different kinds are processed simultaneously in the same reactor (co-processing).

Another advantage of the present invention is that it provides a process of enzymatic hydrolysis allowing monitoring of, and simple adaptation to, changes in the reaction medium without the need for complex measures.

According to a variant, the final content of dry matter is higher than 12% by weight, and preferably between 18 and 24% by weight.

According to a variant, the addition of the enzymes to the reactor is carried out sequentially and increasingly distributed over time.

According to a variant, the pre-treated lignocellulosic substrate and the enzymes are added at the same time to the reactor.

According to a variant, with each addition the pre-treated lignocellulosic substrate is added in the same amount.

According to a variant, with each addition, the enzymes are added in the same amount.

According to a variant, the reactor comprises a stirrer and the ratio of the diameter of the agitator to the diameter of the reactor D:T is between 0.3 and 0.75.

According to a variant, the stirrer is an inclined blade impeller or marine impeller.

According to a variant, the enzymes are brought into contact with a concentration of between 0.1 and 60 mg of enzymes per gram of cellulose.

According to a variant, the process takes place at a temperature of between 40 and 60° C., at a pH of between 4 and 6, and at atmospheric pressure.

According to a variant, various pre-treated lignocellulosic substrates are used, on their own or as a mixture.

According to a variant, said process is followed by a fermentation step in the presence of an alcohol-producing microorganism.

According to another variant, said process is carried out in the presence of an alcohol-producing microorganism according to a process of simultaneous saccharification and fermentation known as a SSF process.

DETAILED DESCRIPTION OF THE INVENTION

The pre-treated lignocellulosic biomass is obtained from wood (deciduous and resinous), raw or treated, by-products of agriculture such as straw, plant fibres, forestry crops, alcohol-, sugar- and cereal-producing plant residues, resides from the paper industry, marine biomass (such as macroalgae cellulosic residue) or lignocellulosic material conversion products.

The lignocellulosic biomass used is preferably wood, wheat straw, wood pulp, miscanthus, rice straw or corn stalks.

According to the process of the invention, the various types of lignocellulosic biomass may be used on their own or as a mixture.

The lignocellulosic substrates used in the process of the invention are the result of pre-treating the biomass under conditions that allow a restructuring of the lignocellulose by modifying the physical and physico-chemical properties of the lignocellulosic material. The pre-treatment step can be carried out using any of the types of pre-treatment of lignocellulosic biomass known to the person skilled in the art. A pre-conditioning step including, by way of example, crushing or stone-removal, may also be carried out. The pre-treatment step may involve heat, chemical, mechanical and/or enzymatic treatment or a combination of these treatments.

According to a preferred variant, the pre-treatment step is selected from among pre-treatment under acid conditions such as acid cooking or steam explosion under acid conditions, pre-treatment in alkaline media such as pre-treatment with sodium sulphide (Kraft process), an ammonia recycle percolation process (ARP) or an ammonia fibre explosion process (AFEX), oxidising pre-treatment such as pre-treatment with ozone, hydrogen peroxide, oxygen or peracetic acid, pre-treatment without the addition of chemical reagents such as steam explosion without addition of acid or pre-treatment by washing with very hot water, or also an organosolv process.

The pre-treatment step is advantageously a pre-treatment by steam explosion under acid conditions. Under optimum conditions of 150 to 250° C. for a few minutes.

The present invention relates to a sequentially fed process of enzymatic hydrolysis in which, under agitation, a pre-treated lignocellulosic substrate is brought into contact with the water and enzymes in a reactor, said process being characterised in that the sequential addition to the reactor of the pre-treated lignocellulosic substrate is carried out increasingly spread out over time, in order to obtain a predetermined final content of dry matter.

The predetermined final content of dry matter is preferably higher than 12% by weight, preferably between 15 and 30% by weight, and most preferably between 18 and 24% by weight. Throughout the remainder of the text, the concentration of pre-treated lignocellulosic substrate is expressed as a percentage by weight of dry matter. The content of dry matter is measured according to standard ASTM E1756-08 (2015) "Standard Test Method for Determination of Total Solids in Biomass".

The content of dry matter at the start of the hydrolysis process, at the time of the first addition of the pre-treated lignocellulosic substrate, is generally below 10% by weight, preferably below 8% by weight and particularly preferably below 6% by weight.

The frequency of addition of the pre-treated lignocellulosic substrate is, increasingly spread out. Thus, additions that are "increasingly spread out over time" means that the additions are made with a decreasing frequency or, put another way, with an increasing cycle. So, the time elapsing between additions n and n+1 is less than the time elapsing between addition n+1 and addition n+2, and so on. For example, the time elapsing between the first and the second addition of substrate is less than the time elapsing between the second and third additions, and so on. By way of example, the first addition may take place after 1 hour, the second after 3 hours, the third after 6 hours, the fourth after 13 hours and the fifth after 24 hours.

In order to reach the predetermined final content of dry matter, generally, and in an increasingly spread out manner, at least 3 additions of substrate are made, preferably at least 4 additions of substrate, and more preferably again at least 5 additions of substrate.

The quantities added at the time of an addition of pre-treated lignocellulosic substrate generally represent an increase in the content of dry matter of at most 5% by weight, preferably of between 2 and 5% by weight, and more preferably again between 2 and 3% by weight. The quantity of substrate added at the time of an addition represents, for example, 3% by weight of dry matter content.

According to a variant, the pre-treated lignocellulosic substrate is added in an equal quantity with each addition.

According to a preferred variant, the addition of the enzymes to the reactor is carried out sequentially and increasingly spread out over time. It has been observed that the addition of enzymes in spread-out, fed-batch, mode allows maintenance of enzymatic activity over time, unlike the addition of all the enzymes at the start of the enzymatic hydrolysis.

The pre-treated lignocellulosic substrate and the enzymes can be added at the same time, or staggered, to the reactor, while continuing the sequential addition increasingly spread out over time of each of the components. The pre-treated lignocellulosic substrate and the enzymes are preferably added at the same time to the reactor.

According to a variant, the enzymes are added in an equal quantity with each addition.

The quantities added at the time of an addition are generally between 0.1 and 60 mg of enzymes per gram of cellulose, preferably between 5 and 40 mg of enzymes per gram of cellulose and most preferably between 10 and 30 mg of enzymes per gram of cellulose.

The enzymatic hydrolysis is generally carried out at a pH of between 4 and 6, preferably between 4.5 and 5.8 and more preferably again between 4.8 and 5.5. It generally takes place at a temperature of between 40 and 60° C., and preferably between 45 and 55° C. It advantageously takes place at atmospheric pressure.

The enzymatic hydrolysis is carried out by means of enzymes produced by a microorganism. The enzymatic solution added contains enzymes that break down the cellulose into sugars. Microorganisms, such as fungi of the genus *Trichoderma, Aspergillus, Penicillium* or *Schizophyllum*, or anaerobic bacteria of, for example, the genus *Clostridium*, produce these enzymes, which in particular contain cellulases suited to the extensive hydrolysis of the cellulose. In a highly preferred manner, the cellulolytic enzymes of step d) are produced by the microorganism *Trichoderma reesei*.

According to the invention the period of contact at the time of the enzymatic hydrolysis is between 5 and 200 hours, preferably between 2 and 100 hours, and most preferably between 1 and 50 hours.

Said process according to the present invention can be monitored by measuring over time the value of one of the rheological characteristics of the reaction medium which are advantageously selected from among the viscosity of the reaction medium, the torque of the shaft of the agitation system and the electrical power consumed by the motor. The electrical power consumed by the motor has the notation $P_{elec}$.

During the process of the invention, that is to say during the liquefaction, the viscosity of the reaction medium, the torque of shaft of the agitation system and the electrical power consumed by the motor are rheological characteristics that are of interest from a number of aspects for monitoring the lignocellulosic substrate produced. In fact, these characteristics of viscosity, torque and power are inter-related. The electrical power consumed by the motor $P_{elec}$ is P linked to the mechanical power $P_{mech}$ driving the stirrer shaft.

The electrical power consumed by the motor is a parameter that is conventionally measured and monitored in pilot or industrial installations.

The following formulas define the relationships between the various parameters:

$$P_{mech} = f(P_{elec}),$$

f being a design characteristic of the motor which is specified by the motor constructor.

$$P_{mech} = 2\pi N \cdot C \text{ in which:}$$

N is the speed of agitation in revolutions per second,
C is the torque in N·m,
and $P_{mech}$ is the power in Watts.
During agitation the following relationship applies:

$$P_{mech} = \rho N_p N^3 D^5$$

$\rho$ is the density of the reaction medium in kg·m$^{-3}$
D is the diameter of the stirrer in m, $N_p$ is a characteristic of the stirrer that depends on the geometry of the tank and the flow regime.

During a laminar flow regime, the following relationship applies:

$$N_p = A/Re, \text{ hence } P_{mech} = \rho A N^3 D^5 / Re$$

with A being a constant of the agitation system and Re the Reynolds number with $Re = \rho N D^2 / \bar{\mu}$,
$\bar{\mu}$ is the mean dynamic viscosity measured in Pascal seconds (Pa·s) of the reaction medium with $\bar{\mu} = P_{mech}/(AN^2D^3) = 2\pi C/(AD^3N)$ While the viscosity and torque of the shaft of the agitation system are measurements that are easily accessible on a small scale, the electrical power consumed by the motor $P_{elec}$ is the magnitude most easily measurable on an industrial scale.

In a highly preferred manner, said process according to the present invention is characterised in that a measurement is performed over time of the electrical power consumed by the motor.

Said process according to the present invention is advantageously carried out in a reactor, preferably with a cylindrical shape, with a height/diameter ratio which is advantageously in the range 1 to 3.

Thanks to the increasingly spread-out fed-batch mode, the effect of the viscosity is less marked in the reaction medium. Conventionally, the stirrer selected must be capable of processing laminar flows. Wide stirrers, or even those which scrape the wall of the reactor at moderate speeds of rotation and applying a blending and kneading action are then necessary. In the process according to the invention, simpler stirrers, of the inclined blade impeller or also marine impeller type, may be used.

In particular, stirrers may be used in the process according to the invention that have a smaller diameter. According to a variant, the stirrer diameter/reactor diameter ratio D/T is advantageously between 0.3 and 0.75, and preferably between 0.4 and 0.65.

Similarly, the speed of rotation can be lower than in the conventional system. The speed of rotation is generally lower than 100 rpm (rotations per minute), preferably lower than 80 rpm.

According to a preferred embodiment, the process of enzymatic hydrolysis according to the invention can be followed by a step of alcoholic fermentation by an alcohol-producing microorganism in order to produce a fermented effluent containing alcohol.

The enzymatic hydrolysis and the alcoholic fermentation can also be performed simultaneously. It is a case here of a simultaneous saccharification and fermentation or SSF process. The enzymatic hydrolysis and the alcoholic fermentation can also be implemented according to other arrangements known to the person skilled in the art, such as the presacchararification followed by simultaneous saccharification and fermentation process (PSSF) or also the hybrid hydrolysis and fermentation process (HHF).

The sugars obtained by enzymatic hydrolysis can be fermented into alcohols such as ethanol, 1,3-propanediol, isopropanol, 1-butanol, isobutanol or 1,4-butanediol, on their own or as a mixture. The alcoholic fermentation preferably produces ethanol.

The alcoholic fermentation is ensured by yeast or other alcohol-producing microorganisms. Within the meaning of this invention, the term "alcoholic fermentation" designates a process of fermentation of the sugars into alcohol (s) by means of microorganisms alone. The alcohol-producing microorganisms used during the alcoholic fermentation step of the hexoses are preferably selected from among yeast and bacteria, which may have been genetically modified.

When the alcohol-producing microorganism is a yeast, *Saccharomyces cerevisiae* is the most effective. It is also possible to select yeasts such as *Schizosaccharomyces pombe* or *Saccharomyces uvarum* or *diastaticus*. More thermophilic yeasts, such as *Kluyveromyces fragilis* (now often designated by *K. marxianus*) are also of interest, particularly when the enzymatic hydrolysis and the alcoholic fermentation are performed simultaneously (SSF process).

A genetically modified organism, such as for example a yeast of the *Saccharomyces cerevisiae* type such as TMB 3400 (Ohgren et al, J. of Biotech 126, 488-498, 2006) may also be used.

When the alcohol-producing microorganism is a bacterium, preference will be for *Zymomonas mobilis* which offers an effective means of assimilation for the production of ethanol, or anaerobic bacteria of the genus *Clostridium*, such as for example *Clostridium acetobutylicum* for the production of mixtures of alcohols and solvents such as acetone-butanol-ethanol (ABE) or isopropanol-butanol-ethanol (IBE), or also *Escherichia coli* for the production of isobutanol, for example.

The alcoholic fermentation is preferentially carried out at a temperature of between 30° C. and 40° C., and a pH of between 3 and 6.5.

Yeasts, and preferably *Saccharomyces cerevisiae* are the highly-preferred microorganisms used. They have greater robustness and safety and do not require sterile conditions to operate the process and plant.

Yeasts of the genus *Saccharomyces* are capable of fermenting solely hexoses (essentially glucose and mannose). These yeasts upgrade hexoses into ethanol in an optimum manner and allow good conversion yields to be obtained.

When the enzymatic hydrolysis and the alcoholic fermentation are carried out in the same operation (SSF process), the temperature is preferably between 30 and 45° C., and the pH between 4 and 6 in order to stimulate the performance of the yeasts. Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 1759033, filed Sep. 28, 2017 are incorporated by reference herein.

The operational example below is intended to illustrate the invention.

EXAMPLES

A process of enzymatic hydrolysis of pre-treated wheat straw with a high content of dry matter (DM) was carried out by sequential feeding (fed-batch) in an increasingly spread out manner. Unlike conventional fed-batch strategies, where the additions are at regular time intervals, this new strategy consists of sequentially increasing the content of dry matter with additions that are increasingly spread out over time. FIGS. 1a and 2a show additions according to the conventional fed-batch technique, while FIGS. 1b and 2b show additions according to the fed-batch technique that are increasingly spread out over time. FIG. 2 expand on the detail of FIG. 1 across the time scale.

All the water content (1.3 kg) and a first addition of pre-treated wheat straw substrate (250 g), sufficient to achieve a concentration of 5% by weight of dry matter, are loaded in the reactor at the start of the test. Then, five equal additions of 170 g of lignocellulosic substrates are made after 1, 3, 6, 13 and 24 hours to achieve 20% by weight of dry matter (FIGS. 1b and 2b). The addition of the enzymes was carried out in the same way. With this strategy, a gradual liquefaction of the substrate particles is possible, without exceeding the critical viscosity value, as this would not allow adequate mixing with inclined blade or also marine impellers.

The process according to the invention allows a yield of glucose of 80 to 85% to be achieved, with a low energy consumption of between 35-40 kJ over 48 h of enzymatic hydrolysis. In particular, the energy consumption achieved by the process of the invention over 48 h was the same as that achieved in just 5 h with other fed-batch strategies. In fact, an exponential increase in glucose is observed in the first 24 hours of the test, when there is intense activity in the conversion of the cellulose by the cellulase. Thereafter, the increase slows: in the first few hours, an increase of 50 to 90 g of glucose was recorded for each kJ consumed in the mixture; after 24 hours, it was 10-15 g/kJ and after 48 h, it had dropped to less than 10 g/kJ.

Similarly, the speed of rotation of the mixing system was slow (approximately 80 rpm). The enzymes are proteins with a molecular structure, stabilised by weak forces. This weak stabilisation means that the proteins are affected by various parameters. Mechanical stress is a factor that can reduce enzymatic activity.

The strategy of sequential additions increasingly spread out over time can also be adopted for the enzymes. FIG. 3 shows the difference between an addition of the full quantity of enzymes at the start of the test (ZE, FIG. 3) and sequential additions, concomitantly with the sequential additions of the substrates (GE, FIG. 3).

FIG. 3 shows that there is a very rapid increase in glucose if the full quantity of enzymes (52.8 g) is fed-in at the start of the enzymatic hydrolysis. However, this means that the glucose is produced too quickly in the reaction medium which inhibits the enzymes and consequently the production of glucose. In contrast, the progressive addition of enzymes (8.8 g for each addition, increasingly spread out over time) allows the inhibited enzymes to be replaced and a higher production of glucose at the end of the process to be obtained (FIG. 3).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

Figure 1A:
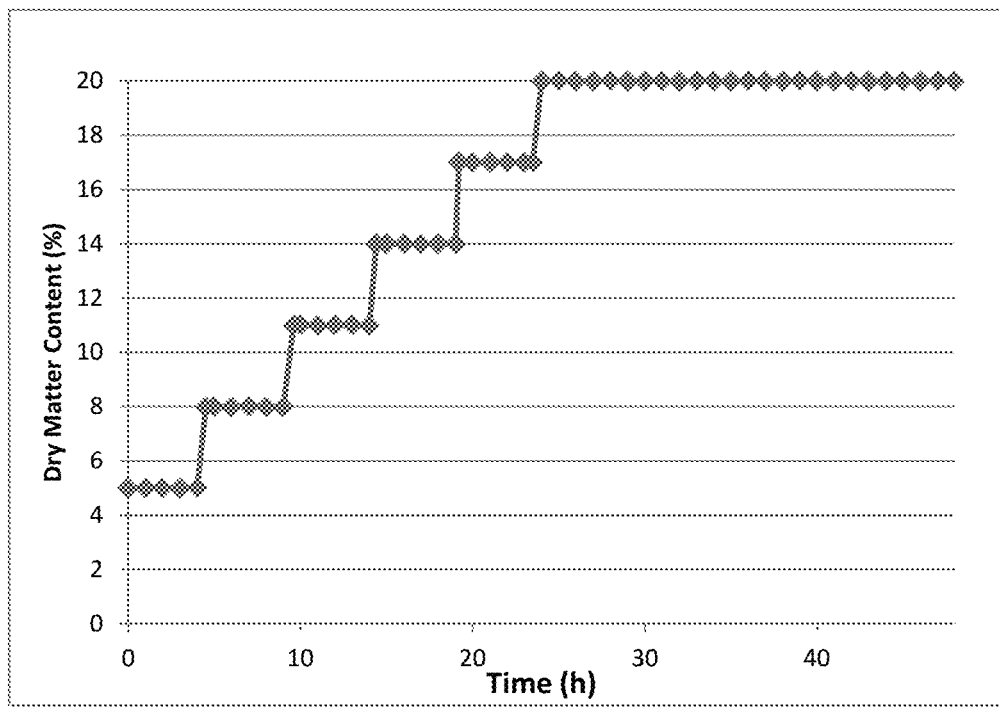
FIG. 1a: shows additions according to the conventional fed-batch technique.
Figure 1B:
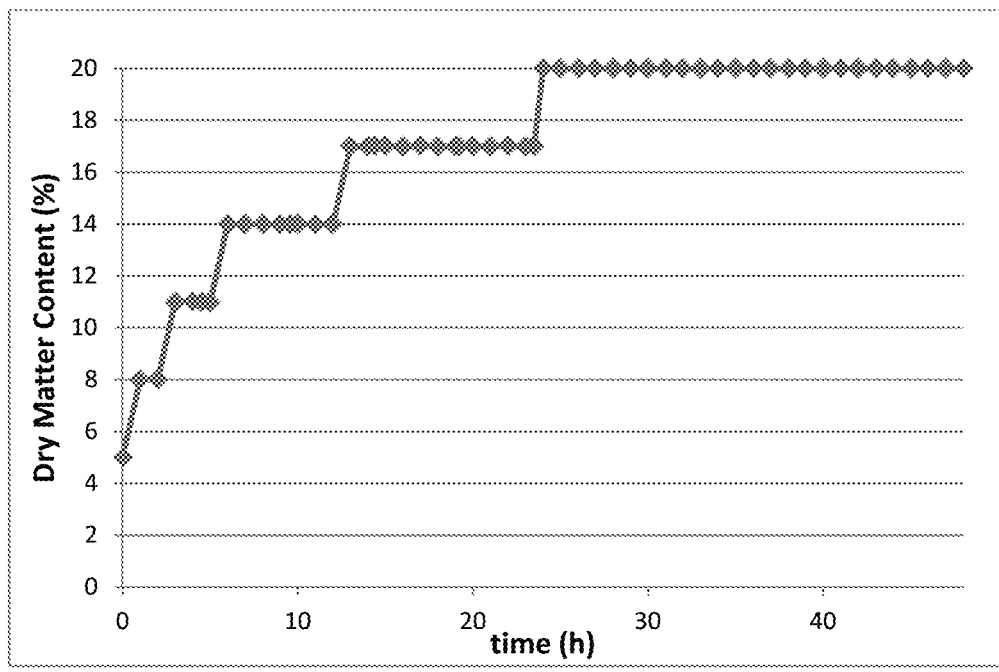
FIG. 1b: shows additions according to the fed-batch technique that is increasingly spread out over time.
Figure 2A:
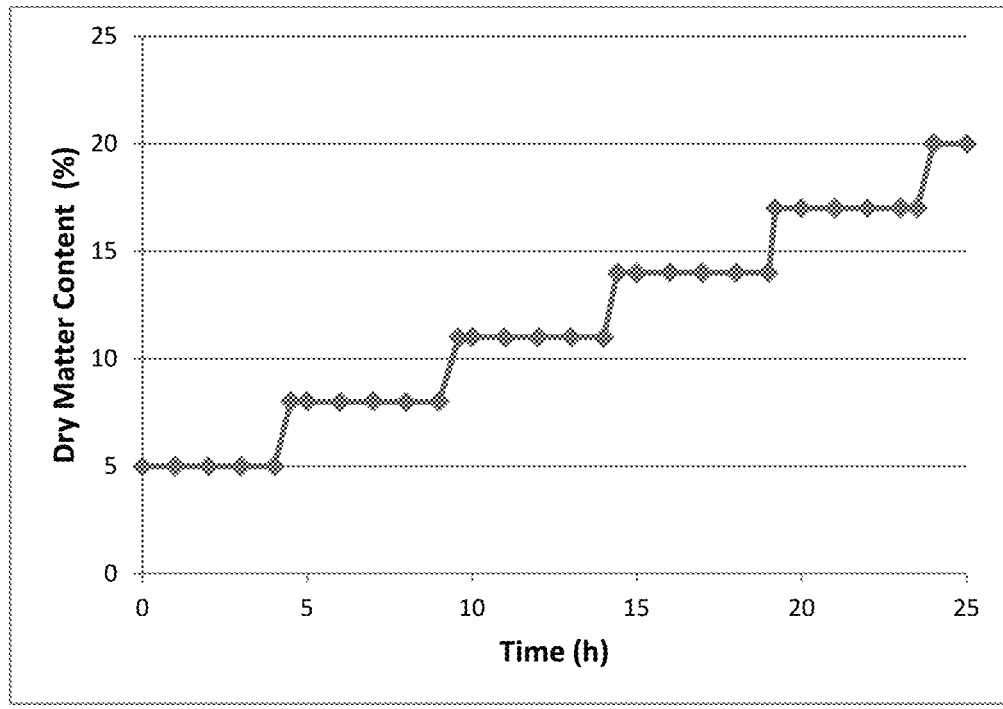
FIG. 2a: shows additions according to the conventional fed-batch technique.
Figure 2B:
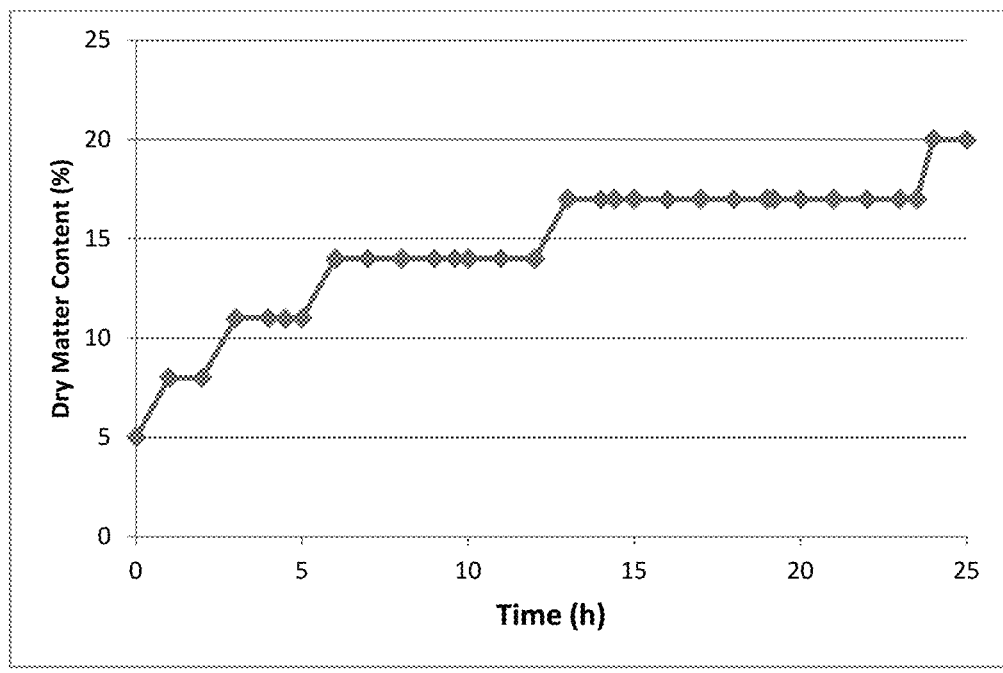
FIG. 2b: shows additions according to the fed-batch technique that is increasingly spread out over time.
Figure 3:
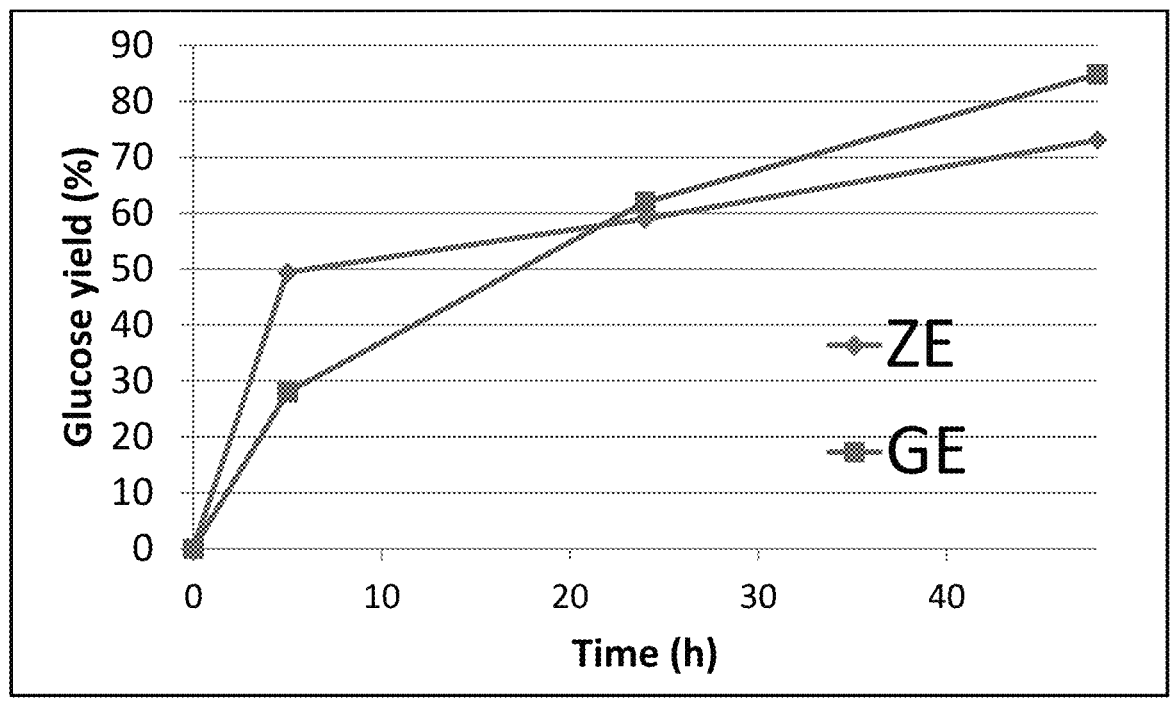
FIG. 3: shows the difference between an addition of the full quantity of enzymes at the start of the test (ZE) and sequential additions, concomitantly with the sequential additions of the substrates (GE).

The invention claimed is:

1. A process for enzymatic hydrolysis of pre-treated lignocellulosic substrate, comprising bringing into contact, under agitation, at least one pre-treated lignocellulosic substrate, which comes from raw or treated wood, marine biomass or a by-product of agriculture, with water and with enzymes in a reactor, comprising adding the at least one pre-treated lignocellulosic substrate to the reactor in a sequential batch-wise manner such that intervals between additions of batches are longer over time within the same process, and obtaining a predetermined final content of dry matter that is higher than 12% by weight.

2. The process according to claim 1, in which the final content of dry matter is 17 to 30% by weight.

3. The process according to claim 1, in which the final content of dry matter is between 18 and 24% by weight.

4. The process according to claim 1, in which the addition of the enzymes to the reactor is carried out sequentially and increasingly spread out over time.

5. The process according to claim 1, in which the pre-treated lignocellulosic substrate and the enzymes are added at the same time to the reactor.

6. The process according to claim 1, in which, with each addition, the pre-treated lignocellulosic substrate is added in the same amount.

7. The process according to claim 1, in which, with each addition, the enzymes are added in the same amount.

8. The process according to claim 1, in which the reactor comprises a stirrer and the ratio of the diameter of the stirrer to the diameter of the reactor D:T is between 0.3 and 0.75.

9. The process according to claim 1, in which the reactor comprises a stirrer, which is an inclined blade impeller or marine impeller.

10. The process according to claim 1, in which the enzymes have a concentration of between 0.1 and 60 mg of enzymes per gram of cellulose.

11. The process according to claim 1, in which the process takes place at a temperature of between 40 and 60° C., at a pH of between 4 and 6, and at atmospheric pressure.

12. The process according to claim 1, in which various pre-treated lignocellulosic substrates are processed, on their own or as a mixture.

13. The process according to claim 1, which is followed by fermentation in the presence of an alcohol-producing microorganism.

14. The process according to claim 1, which is carried out in the presence of an alcohol-producing microorganism according to a process of simultaneous saccharification and fermentation.

15. A process for enzymatic hydrolysis of pre-treated lignocellulosic substrate, comprising bringing into contact, under agitation, at least one pre-treated lignocellulosic substrate with water and with enzymes in a reactor, comprising adding the at least one pre-treated lignocellulosic substrate to the reactor in a sequential batch-wise manner such that intervals between additions of batches are longer over time within the same process, and obtaining a predetermined final content of dry matter that is higher than 12% by weight, wherein the at least one pre-treated lignocellulosic substrate comes from raw or treated wood, or a by-product of agriculture.

16. A process for enzymatic hydrolysis of pre-treated lignocellulosic substrate, comprising bringing into contact, under agitation, at least one pre-treated lignocellulosic substrate, which is not from paper industry, with water and with enzymes in a reactor, comprising adding the at least one pre-treated lignocellulosic substrate to the reactor in a sequential batch-wise manner such that intervals between additions of batches are longer over time within the same process, and obtaining a predetermined final content of dry matter that is higher than 12% by weight.

17. The process according to claim 16, in which the final content of dry matter is 17 to 30% by weight.

* * * * *